Figure 1:
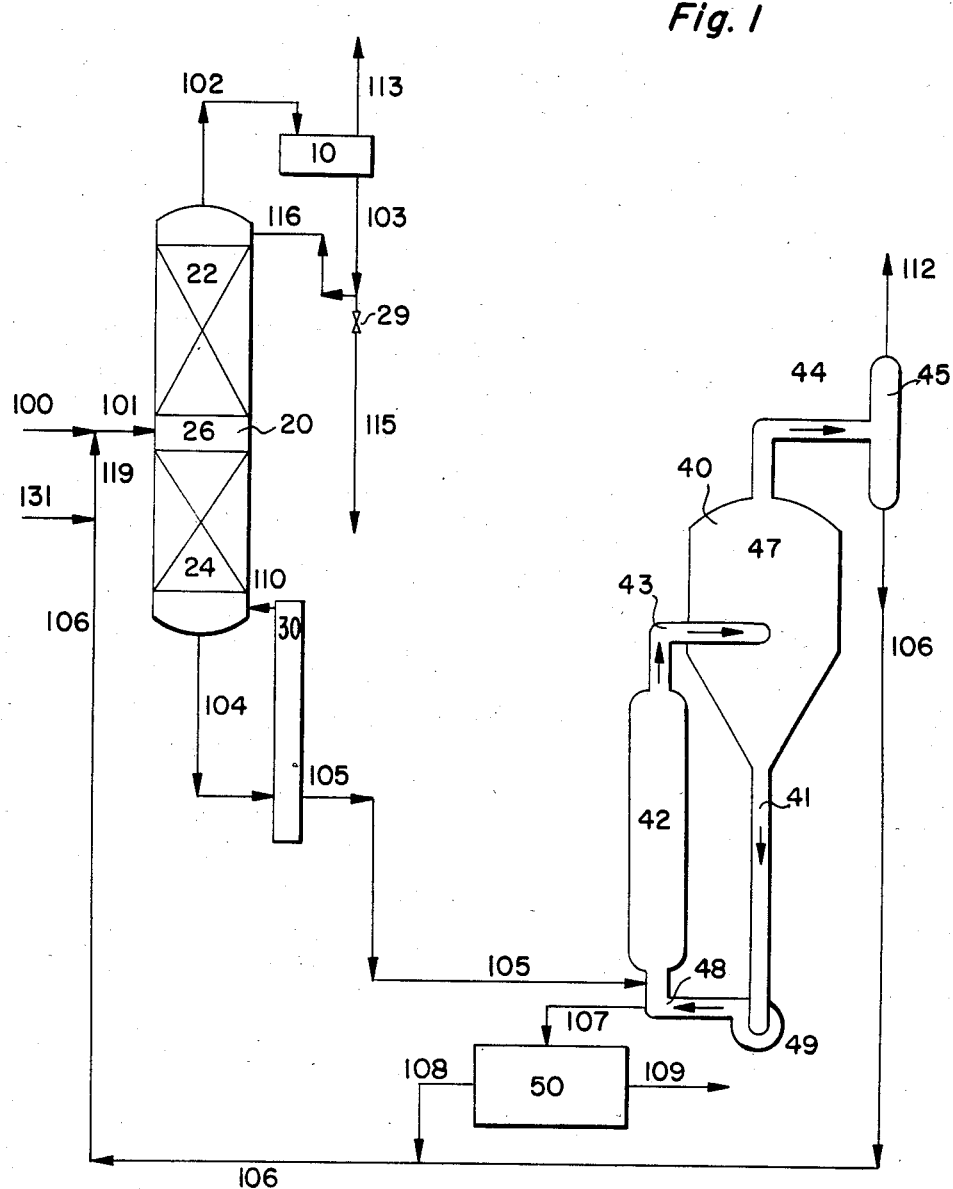

United States Patent [19]

Dodge

[11] Patent Number: 4,567,258

[45] Date of Patent: Jan. 28, 1986

[54] PROCESS AND APPARATUS FOR PRODUCING CYANURIC ACID

[75] Inventor: William B. Dodge, Montgomery Township, Somerset County, N.J.

[73] Assignee: Olin Corporation, Cheshire, Conn.

[21] Appl. No.: 724,730

[22] Filed: Apr. 18, 1985

[51] Int. Cl.$^4$ .................................. C07D 251/32
[52] U.S. Cl. ............................................ 544/192
[58] Field of Search .................................. 544/192

[56] References Cited

U.S. PATENT DOCUMENTS

| | | | |
|---|---|---|---|
| 2,943,088 | 6/1960 | Westfall | 260/248 |
| 3,563,987 | 2/1971 | Berkowitz | 260/248 |
| 3,954,751 | 5/1976 | Fuchs et al. | 260/248 A |
| 4,167,631 | 9/1979 | Schouteten et al. | 544/192 |
| 4,220,769 | 9/1980 | Smialek et al. | 544/192 |
| 4,266,052 | 5/1981 | de Cooker et al. | 544/192 |
| 4,294,962 | 10/1981 | Bagnall et al. | 544/192 |
| 4,356,303 | 10/1982 | Wojtowicz | 544/192 |

*Primary Examiner*—John M. Ford
*Attorney, Agent, or Firm*—F. A. Iskander

[57] ABSTRACT

A process is provided to produce a solution or slurry of cyanuric acid in an inert solvent essentially free from by-product impurities from an aqueous solution of urea and/or biuret. Optionally, the cyanuric acid product may be separated from the inert solvent by filtering, centrifuging or distilling off the inert solvent and leaving the cyanuric acid solid.

26 Claims, 2 Drawing Figures

PROCESS AND APPARATUS FOR PRODUCING CYANURIC ACID

The invention relates to an improved process and apparatus for producing cyanuric acid, and particularly for converting an aqueous solution of urea or biuret to cyanuric acid.

It is well-known that urea is produced by a high temperature, high pressure reaction of ammonia and carbon dioxide. The urea is initially produced as an aqueous solution containing about 76% urea which solution can be readily concentrated to contain about 90% to 96% urea. Further dehydration to form solid urea prills or granules is expensive and frequently results in both decomposing urea and increasing the biuret concentration so that the urea is not suitable for some fertilizer applications.

It is also well-known that urea or biuret or a mixture thereof can be pyrolyzed at temperatures of about 180° C. and higher to form cyanuric acid. The pyrolysis can be carried out in a kiln, as described in U.S. Pat. No. 2,943,088 to Westfield, or in an inert organic solvent as described in U.S. Pat. No. 3,563,987, the teachings of the latter are incorporated herein by reference. In the preparation of cyanuric acid by pyrolysis in an inert organic solvent, it was heretofore necessary to avoid aqueous urea as a raw material but instead to dissolve prills or granules of urea or biuret in the solvent prior to heating so that a temperature of 180° C. could be attained without flashing water off violently and without excessive foaming which could result in the loss of both the solvent and urea or biuret as well as to avoid decomposing the urea.

An object of the present invention is the provision of an improved and more satisfactory process and apparatus for producing cyanuric acid.

Another object of the invention is the provision of an improved process and apparatus for converting a source of raw material comprising an aqueous solution of urea and/or biuret to a solution or slurry of cyanuric acid in an inert solvent from which such cyanuric acid may be readily recovered.

Still another object of the invention is an improved process and apparatus by which water of an aqueous solution of urea and/or biuret is exchanged with an inert organic solvent, and the resulting organic solution of urea and/or biuret is pyrolyzed to form cyanuric acid in the inert organic solvent as a solution or slurry and from which it may be readily separated.

Stated briefly, the apparatus and process of the present invention facilitate the production of cyanuric acid as a solution or slurry in an inert organic solvent by the pyrolysis of a compound consisting essentially of urea and/or biuret initially dissolved as an aqueous solution.

The apparatus of the present invention comprises a system for the continuous conversion of urea and/or biuret to cyanuric acid and includes a condenser, distillation vessel, crystallizer, and at least one heater which cooperates with the crystallizer to provide a recycle loop within which the inert solvent solution of urea and/or biuret is pyrolyzed to provide for a solution or slurry of cyanuric acid in the inert organic solvent. In one of the two preferred embodiments of the apparatus hereafter described in detail, a second heater is utilized as a reboiler to vaporize sufficient inert organic solvent to provide essentially complete replacement of the water of the aqueous solution of urea and/or biuret with the inert organic solvent prior to the entry of the resulting solution into the recycle loop. In the other embodiment, the distillation vessel is open to the crystallizer so that the heater of the recyle loop serves the dual function of vaporizing sufficient inert organic solvent to provide for an essentially complete replacement of the water of the aqueous solution of urea and/or biuret by the inert organic solvent vapor and, subsequently, pyrolyzing urea and/or biuret to form the solution or slurry of the cyanuric acid in such inert solvent.

In the process, the aqueous solution of urea and/or biuret and the inert organic solvent are continuously delivered, either together or separately, into a feed zone of the distillation vessel, which feed zone is located between a rectifying zone and a stripping zone within the distillation vessel. Within this feed zone, the mixture of an aqueous solution of urea and/or biuret and inert organic solvent are combined with a reflux liquid which is provided by condensing vapors from the combined solution after the vapors have passed through the distillation vessel and into the condenser.

The vapors issuing from the combined solution are generated by contacting vapors of inert organic solvent introduced into the bottom of the stripping zone. It is within the stripping zone that substantially all of the water in the combined solution is evaporated by contacting and condensing vapors of inert organic solvent. Similarly, substantially all of the vapor of the inert organic solvent entering the rectifying zone is condensed by contacting the aqueous reflux in the distillation vessel. As a consequence, the solution conveyed from the stripping zone of the distillation vessel comprises a substantially water-free solution of urea and/or biuret in an inert organic solvent, which solution is conveyed to the crystallizer.

In one embodiment of the invention, the solution from the distillation vessel is first conveyed through a heater or reboiler in which some of the inert organic solvent is vaporized and delivered to the stripping zone to evaporate water from the combined solution passing therethrough. In the other embodiment, the solution from the stripping zone is discharged directly into the crystallizer and inert organic solvent vapors from the solution in the crystallizer is delivered to the stripping zone to evaporate water from the combined solution as described above.

In both embodiments, the crystallizer and a crystallizer heater, together with suitable recirculation means, such as a pump means or a draft tube means, form a recycle loop in which the heater maintains the resulting solution at a pyrolyzing temperature of not less than about 180° C., desirably at 200° C. or higher, and preferably between 210° C. and 250° C. At such temperatures, the urea and/or biuret in the crystallizer is converted to cyanuric acid and ammonia. The ammonia is vaporized and, together with any inert organic solvent vapor, is continuously withdrawn.

In one embodiment of the invention, such vapors are passed through the distillation vessel to evaporate water from the combined solution in the stripping zone as described above. In another such embodiment, the ammonia vapors and inert organic solvent vapors are passed through a separate condenser with the condensed inert organic solvent being collected, and more preferably, returned as part of the inert organic solvent introduced into the distillation feed zone. In both of these embodiments, any vaporized ammonia is exhausted from the respective condensers, and the cyanuric acid that is formed remains as a solution or slurry in the inert organic solvent. A portion of this recycled solution or slurry of cyanuric acid is continuously or periodically removed as a side stream from which the cyanuric acid is separated and the remaining inert organic solvent being recycled as part of the feed stream to the distillation vessel.

Suitable for use in the process of the present invention is any organic solvent having a vapor pressure less than the vapor pressure of water, which is capable of dissolving urea and biuret in substantial quantities, which remains stable at the temperature encountered in the described process, and which remains inert with respect to the reactants and products at the reaction temperature. The boiling point of any liquid is known to vary with pressure. If the boiling point of the inert organic solvent is greater than 180° C. at one atmosphere, it is convenient to operate the system under a subatmospheric pressure to rapidly remove the ammonia formed during the pyrolysis step while maintaining the reaction temperature of not less than about 180° C. Alternatively, it may be desirable to operate the system at atmospheric or superatmospheric pressures to obtain the necessary reaction temperature of not less than about 180° C. and to provide sufficient vapors of the inert organic solvent to evaporate the water from the combined solution. Inert organic solvents suitable for use in the process of the invention include dialkyl sulfones or cyclic sulfones with at most 12 carbon atoms, halogen-substituted cresols and phenols, pyrrolidones and N-substituted urethanes with phenyl or alkyl groups with at most 6 carbon atoms, cyclic urethanes, polyether alcohols and cyclic polyethers and cyclohexanol or substituted cyclohexanols with one or more hydrocarbon groups with, at most 6 carbon atoms as substituents. The hydrocarbon groups are preferably phenyl-, alkyl- or cycloalkyl groups. Specific examples of such suitable inert organic solvents are dimethyl sulfone, dipropyl sulfone, sulfolane, chlorocresols, 5-methyl-2-oxazolidinone, diethyleneglycol monomethyl ether, diethyleneglycol diethyl ether, 2-methyl cyclohexanol, 2,6-dimethyl cyclohexanol and 2,4,6-trimethyl cyclohexanol. A particularly suitable inert solvent is sulfolane, tetramethylene sulfone. When sulfolane is employed as the inert solvent, it is desirable to operate the crystallizer means under subatmospheric pressures of up to about 33 kPa (250 mm Hg) to thereby rapidly remove ammonia from the solution.

Although the quantity of water used in preparing the aqueous solution of urea and/or biuret is not critical, it is economically desirable that such solution contains between 8% and 4% water. If the quantity of water is greater than 8%, it is easier and less expensive to evaporate the water from the aqueous solution by conventional means. On the other hand, the dehydration of the solution to contain less than 4% water by conventional means offers no economic advantage and may result in decomposing some of the urea. The water is replaced with the inert solvent in the distillation vessel by controlling the aqueous reflux liquid introduced into the rectifying zone and the vapors introduced into the stripping zone.

It is critical to prevent solid cyanuric acid from forming in the stripping zone, accumulating on surfaces thereof, and obstructing the flow of solution to the crystallizer. This can be accomplished by maintaining the temperature of the stripping zone sufficiently low; that is, below about 180° C., so that there is little or no conversion of urea or biuret to cyanuric acid while solution is in the stripping zone. Maintaining a temperature of the solution up to about 220° C. in the stripping zone normally can be tolerated for only a short time without forming solid cyanuric acid deposits.

In one preferred embodiment of the apparatus of the present invention, one heater is a reboiler for the distillation vessel and the crystallizer comprises a continuous forced circulation crystallizer with a recycle loop including a second heater such as taught by Bagnall et al. in U.S. Pat. No. 4,294,962 which is incorporated herein by reference.

The solution of urea and/or biuret in the inert organic solvent is circulated at high velocity through the recycle loop and is maintained at a temperature of not less than 180° C. or higher thereby forming a solution or slurry of cyanuric acid in the inert organic solvent. The crystallizer heretofore mentioned is maintained at subatmospheric pressure and the solution or slurry is introduced therein in a manner as to maximize agitation of the solution or slurry of cyanuric acid.

Figure 2:
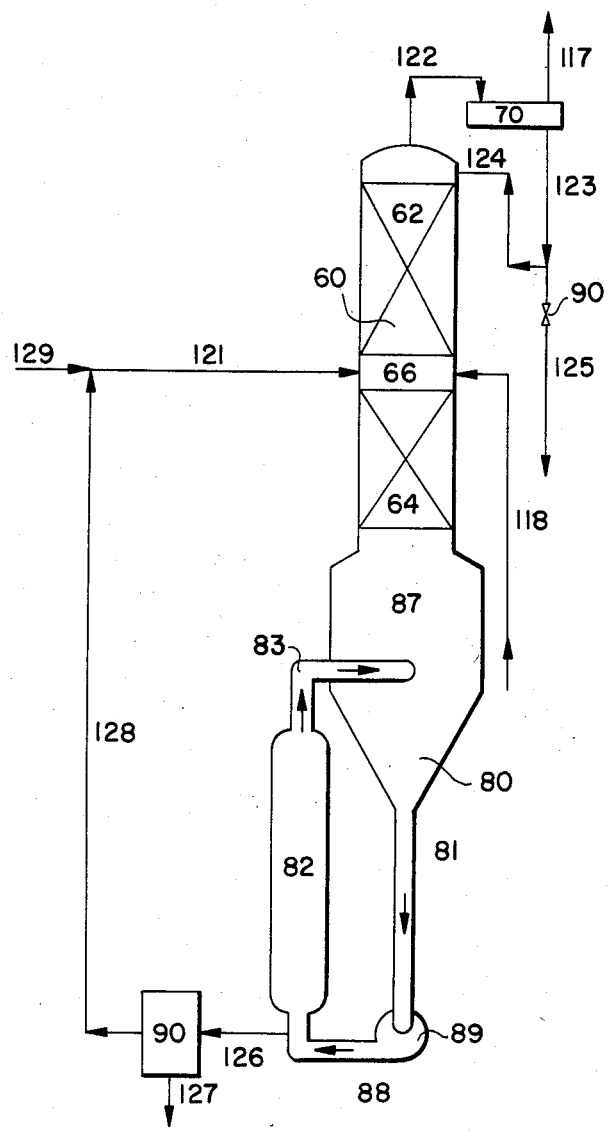

For a more detailed description of the present invention, reference is made to the accompanying drawings in which:

FIG. 1 is a diagrammatic illustration of one preferred embodiment of the apparatus of the invention in which material flow are indicated to afford a better understanding of the process of this invention; and FIG. 2 is a view similar to that of FIG. 1 diagrammatically illustrating another preferred embodiment of the invention.

With respect to FIG. 1, character 20 denotes a distillation vessel comprising a feed zone 26 between an upper rectifying zone 22 and a lower stripping zone 24. Above the rectifying zone 22, conduit or line 102 connects the distillation vessel 20 to condenser 10 which is connected by line 113 to a source of lower pressure, such as a vacuum pump, not shown, whereby vapors from the distillation vessel 20 are drawn into the condenser 10. Liquid condensate, water, is conducted from the condenser 10 by line 103 to line 116, which connects to distillation vessel 20 above rectifying zone 22, and to valve 29, which valve controls the fraction of condensate which returns to the distillation vessel as relux; the balance of the condensate is conveyed to discard through line 115.

The reflux flows downward through rectifying zone 22 of the distillation vessel 20 into feed zone 26. Feed zone 26 also receives both an aqueous urea and/or biuret solution from a supply source, not shown, through lines 101 and 100, and also an inert organic solvent through lines 101 and 119. The aqueous solution and solvent combine with the reflux to form a combined solution that flows downward through stripping zone 24. The combined solution is conducted from the bottom of distillation vessel 20 by line 104 to a heater or reboiler 30, within the reboiler 30 part of the inert organic solvent is vaporized and is conducted into distillation vessel 20 below the stripping zone 24 by line 110; the balance of the combined solution is conducted from reboiler 30 to the crystallizer section 40 which is discussed later.

In operation, aqueous urea and/or biuret feed from line 100 and inert organic solvent from line 119 are conducted by line 101 into feed zone 26 where, with the reflux, a combined solution is formed which flows into stripping zone 24 countercurrent to sufficient inert organic solvent vapor from reboiler 30 to evaporate substantially all the water from the combined solution. Water-enriched vapor emerging from the top of stripping zone 24 is drawn through feed zone 26 into rectifying zone 22 where it contacts the reflux therein. Sufficient reflux is provided by adjusting valve 29 to condense substantially all of the inert organic solvent from the vapor within rectifying zone 22.

Crystallizer 40 comprises a reaction chamber 47 with a recycle loop comprising intake conduit or line 41 at the bottom of reaction chamber 47, pump 49, line 48, crystallizer heater 42, and return line 43 which is connected to reaction chamber 47 below the top thereof. Conduit or line 44 is connected to reaction chamber 47 above line 43 and conducts vapor to condenser 45. Condenser 45 is connected to a source of lower pressure, not shown, by line 112, and to line 119 by line 106. Line 119 is also connected to a solvent make-up tank, not shown, by line 131. Line 48 of the recycle loop is connected to line 105 from reboiler 30 and to separator 50 by line 107. Line 108 which conducts inert organic solvent from separator 50 into line 106 and product cyanuric acid solids are recovered from the separator through line 109.

In operation, combined solution enters the recycle loop prior to the crystallizer heater 42 where it is heated to at least about 180° C., desirably 200° C. or higher, and preferably between 210° C. and 250° C., thereby facilitating conversion of the urea and/or biuret therein into a solution or slurry of cyanuric acid and ammonia. The solution of slurry passes into the reaction chamber 47 where ammonia and any solvent vapor are released and are drawn into condenser 45 where solvent is condensed and is conducted by line 106 to line 119. Ammonia is conducted from the system by line 112. The liquid solution or slurry reenters the recycle loop at inlet line 41 and into line 48 where sufficient solution or slurry is withdrawn through line 107 to maintain the interface between the solution or slurry and vapor in reaction chamber 47 at the desired level, preferably at or about the level of entry of return line 43. The solution or slurry in line 107 enters separator 50 wherein cyanuric acid is delivered to output through line 109 and the balance, primarily inert organic solvent, is conducted by line 108 to line 106 containing solvent from condenser 45 and which, together with make-up solvent from line 131, is used as the solvent fed into feed zone 26.

As with apparatus shown in FIG. 1, the apparatus in FIG. 2 includes a distillation vessel 60, a crystallizer 80, with reaction chamber 87 and a recycle loop comprising conduit 81, pump 89, conduit 88, heater 82, and conduit 83 and a spearator 90, all of which function in essentially the same manner as the corresponding element of the apparatus shown in FIG. 1.

Thus, an aqueous solution of urea and/or biuret is delivered by line 118 into feed zone 66 of distillation vessel 60 along with inert organic solvent introduced into feed zone 66 through line 121 forming a combined solution of urea and/or biuret when combined with reflux, a fraction of the condensate delivered from condenser 70 by line 123 and line 124, into and through rectifying zone 62. The combined solution flows through stripping zone 64 countercurrent to solvent and ammonia vapors from the solution or slurry in crystallizer 80, which solution or slurry is maintained at a temperature of not less than about 180° C., desirably at 200° C. or higher, and preferably between 210° C. to 250° C., thereby converting the combined solution of urea and/or biuret into a solution or slurry of cyanuric acid, ammonia vapor, and sufficient solvent vapor to evaporate substantially all the water from the combined solution.

This solution or slurry of cyanuric acid in crystallizer 80 is withdrawn from line 88 through line 126 to separator 90 as before. There the product, cyanuric acid, is discharged from the system through line 127 while the inert organic solvent is recycled by line 128 to line 121 and, if necessary, supplemented with make-up solvent from storage, not shown, through line 129.

The apparatus shown in FIG. 2 differs from that of FIG. 1 in that the distillation vessel 60 is in direct communication with and discharges into the crystallization reaction chamber 87 a solution of urea and/or biuret in an inert solvent. As this solution is circulated through the recycle loop conduits 81 and 88, pump 89, and heater 82, it is heated and forcefully returned to reaction chamber 87 as described in connection with FIG. 1 and is converted to a solution or slurry of cyanuric acid and ammonia. The ammonia vapor and vapor of the inert organic solvent are conducted into the distillation vessel 60 to evaporate water from the combined solution as heretofore described. The ammonia, together with the water vapor, is exhausted through distillation vessel 60 to condenser 70 wherein the water vapor saturated with ammonia is condensed and the balance of the ammonia vapor is exhausted through line 117 and excess condensate is discharged through line 125.

What is claimed is:

1. A process for the production of cyanuric acid as a solution or slurry in an inert organic solvent by the pyrolysis of a compound selected from the group consisting of urea and/or biuret, said compound being dissolved as an aqueous solution comprising the steps of combining the aqueous solution of the compound with an inert organic solvent to form a combined solution of the compound in a mixed water and inert organic solvent, stripping water from the combined solution as it flows in one direction by contacting the combined solution with a countercurrent flow of vapors of the inert organic solvent thereby providing a solution of the compound in the solvent and a mixed water-inert organic solvent vapor flowing from and countercurrent to said solvent solution of the compound, rectifying the mixed water-inert organic solvent vapor by contacting the same with a countercurrent flow of aqueous reflux to thereby condense substantially all of the inert organic solvent and to provide a flow of aqueous vapors substantially free of the inert organic solvent, condensing said aqueous vapors and introducing a portion thereof as said reflux, heating at least a portion of the solvent solution of the compound to provide said flow of vapors of inert organic solvent countercurrent to and necessary for stripping the water from the combined solution, and maintaining the temperature of the solvent solution of the compound at not less than 180° C. to provide a solution or slurry comprised of cyanuric acid in inert organic solvent.

2. The process of claim 1 with the added step of separating substantially pure cyanuric acid from the solution or slurry.

3. The process of claim 1 wherein the inert organic solvent is sulfolane.

4. The process of claim 1 wherein the temperature of the solvent solution of the compound is maintained at 200° C. or higher.

5. The process of claim 1 wherein the temperature of the compound in the solvent solution is maintained between 210° C. and 250° C.

6. The process of claim 4 with the added step of separating substantially pure cyanuric acid from the solution or slurry.

7. The process of claim 4 wherein the inert organic solvent is sulfolane.

8. The process of claim 5 with the added step of separating substantially pure cyanuric acid from the solution or slurry.

9. The process of claim 5 wherein the inert organic solvent is sulfolane.

10. The process of claim 6 wherein the inert organic solvent is sulfolane.

11. The process of claim 8 wherein the inert organic solvent is sulfolane.

12. A process for the production of cyanuric acid as a solution or sulurry in an inert organic solvent by the pyrolysis of a compound selected from the group consisting of urea and/or biuret, said compound being dissolved as an aqueous solution comprising the steps of:
(a) exchanging the water of the aqueous solution with an inert organic solvent by:
   (i) introducing the aqueous solution of urea and/or biuret into a reaction system comprising a condenser, a distillation vessel, a reboiler, and a crystallizer with a heater, said aqueous solution being introduced into the reaction system at a feed zone of the distillation vessel between a rectifying zone and a stripping zone and said reaction system being maintained at a subatmospheric pressure,
   (ii) introducing the inert organic solvent into the distillation vessel at the feed zone thereby forming a combined solution of the compound in a mixed water and inert organic solvent, said combined solution flowing into the stripping zone,
   (iii) heating effluent from the stripping zone with the reboiler sufficiently to vaporize inert organic solvent, introducing said vapor flowing countercurrent to the flow of the combined solution through the stripping zone thereby vaporizing essentially all of the water which, together with solvent vapor flow into the rectifying zone and the effluent from the stripping zone is essentially free of water,
   (iv) condensing vapor emerging from the rectifying zone and introducing sufficient condensed vapor as reflux into the retifying zone to condense essentially all of the inert organic solvent flowing therethrough,
   (v) maintaining a subatmospheric pressure on the condenser sufficient to maintain a vapor flow into and through the distillation vessel to the condenser;
(b) passing effluent from the stripping zone to the crystallizer;
(c) maintaining the effluent from the stripping zone in the crystallizer at a temperature of not less than 180° C. by means of a heater thereby forming a solution or slurry of cyanuric acid therefrom; and
(d) separating substantially pure cyanuric acid from the solution or slurry.

13. The process of claim 12 wherein the inert organic solvent is sulfolane.

14. The process of claim 1 wherein the crystallizer comprises a forced circulation crystallizer.

15. The process of claim 12 wherein the crystallizer is maintained at a subatmospheric pressure of up to about 33 kPa (250 mm Hg).

16. A process for the production of cyanuric acid as a solution or slurry in an inert organic solvent by the pyrolysis of a compound selected from the group consisting of urea and/or biuret, said compound being dissolved as an aqueous solution comprising the steps of:
(a) exchanging the water of the aqueous solution with an inert organic solvent by:
   (i) introducing the aqueous solution of urea and/or biuret into a reaction system comprising a condenser, a distillation vessel, and a crystallizer with a heater, said aqueous solution being introduced into the reaction system at a feed zone of the distillation vessel between a rectifying zone and a stripping zone and said reaction system being maintained at a subatmospheric pressure,
   (ii) introducing the inert inorganic solvent into the distillation vessel at the feed zone thereby forming a combined solution of the compound in a mixed water and inert organic solvent, said combined solution flowing into the stripping zone,
   (iii) heating effluent from the stripping zone in the crystallizer sufficiently to vaporize inert organic solvent therefrom to form a vapor, introducing said vapor flow countercurrent to the flow of combined solution through the stripping zone thereby vaporizing essentially all of the water which, together with solvent vapor flow into the rectifying zone and the effluent from the stripping zone is essentially free of water,
   (iv) condensing vapor emerging from the rectifying zone and introducing sufficient condensed vapor as reflux into the rectifying zone to condense vapor essentially all of the inert organic solvent flowing therethrough, and
   (v) maintaining a subatmospheric pressure on the condenser sufficient to maintain a vapor into and through the distillation vessel to the condenser; and
(b) passing effluent from the stripping zone to the crystallizer;
(c) maintaining the effluent from the stripping zone in the crystallizer at a temperature of not less than 180° C. thereby forming a solution or slurry of cyanuric acid therefrom; and
(d) separating substantially pure cyanuric acid from the solution or slurry.

17. The process of claim 16 wherein the inert organic solvent is sulfolane.

18. The process of claim 16 wherein the crystallizer comprises a forced circulation crystallizer.

19. The process of claim 16 wherein the crystallizer means is maintained at a subatmospheric pressure of up to about 33 kPa (250 mm Hg).

20. An apparatus for the production of cyanuric acid by the pyrolysis of a compound selected from the group consisting of urea and/or biuret dissolved in an inert organic solvent, the compound being initially introduced into the apparatus as an aqueous solution of the compounds, means for delivering vapor of an inert organic solvent into the distillation vessel, the apparatus comprising a distillation vessel having a feed zone into which the aqueous solution is delivered, a stripping zone in which essentially all of the water of the aqueous solution is replaced with inert organic solvent by contacting the aqueous solution with inert organic solvent vapor such that part of the inert organic solvent vapor condenses as a liquid thereby evaporating water from the solution to form a mixed vapor comprised of water and inert organic solvent, and a rectifying zone in which the mixed vaporized water and vaporized inert organic solvent is contacted with a liquid reflux to provide water vapor substantially free from inert organic solvent vapor, a means including a condenser for receiving and condensing water vapor from the distillation vessel and for delivering a portion thereof to the distillation vessel as liquid water reflux, a crystallizer means for conducting the solvent solution of the compound from said distillation vessel and circulating same into and through said crystallizer, means for maintaining said solvent solution of the compound at not less than 180° C. elevated temperature to provide a solution or slurry of cyanuric acid in inert organic solvent, and means for receiving from said crystallizer at least a portion of the solution or slurry of cyanuric acid as it is circulated therethrough.

21. The apparatus of claim 20 wherein the means for delivering inert organic solvent includes a reboiler and the means for maintaining the solvent solution at a predetermined elevated temperature is a heater in the crystallizer.

22. The apparatus of claim 20 wherein the distillation vessel is in direct communication with the crystallizer such that the effluent from the stripping zone of the distillation vessel is discharged directly into the crystallizer and vaporized inert organic solvent is conducted from the crystallizer into the distillation vessel.

23. The apparatus of claim 20 with a separator connected by conduit means to the crystallizer whereby a part of the solution or slurry from the crystallizer is separated into solid cyanuric acid and the balance is directed into the feed zone of the crystallizer.

24. The apparatus of claim 21 with a separator connected by conduit means to the crystallizer whereby a part of the solution or slurry from the crystallizer is separated into solid cyanuric acid and the balance is directed into the feed zone of the crystallizer.

25. The apparatus of claim 22 with a separator connected by conduit means to the crystallizer whereby a part of the solution or slurry from the crystallizer is separated into solid cyanuric acid and the balance is directed into the feed zone of the crystallizer.

26. A process for the production of cyanuric acid comprising the steps of:
(a) combining an aqueous solution of a compound selected from the group consisting of urea, biuret or a mixture thereof with an inert organic solvent to form a combined solution of the compound in a solvent system comprising water and the inert organic solvent,
(b) contacting the combined solution with a countercurrent flow of vapors from the organic solvent to evaporate water therefrom thereby providing a solution or slurry of the compound in the organic solvent, the solution being substantially free of water and a water-enriched vapor,
(c) heating the solution or slurry to a temperature of at least 180° C. to provide a solution or slurry of cyanuric acid in the inert organic solvent, then
(d) separating the cyanuric acid from the inert organic solvent.

* * * * *